US009399309B2

(12) United States Patent
McEntire et al.

(10) Patent No.: US 9,399,309 B2
(45) Date of Patent: Jul. 26, 2016

(54) METHODS FOR THREADING SINTERABLE MATERIALS AND RELATED APPARATUS AND SYSTEMS

(71) Applicant: AMEDICA CORPORATION, Salt Lake City, UT (US)

(72) Inventors: Bryan J. McEntire, Sandy, UT (US); Prabhakar Thirugnanasambandam, Midvale, UT (US)

(73) Assignee: AMEDICA CORPORATION, Salt Lake City, UT (US)

( * ) Notice: Subject to any disclaimer, the term of this patent is extended or adjusted under 35 U.S.C. 154(b) by 159 days.

(21) Appl. No.: 14/070,061

(22) Filed: Nov. 1, 2013

(65) Prior Publication Data
US 2014/0124991 A1 May 8, 2014

Related U.S. Application Data

(60) Provisional application No. 61/721,796, filed on Nov. 2, 2012.

(51) Int. Cl.
*B28B 11/08* (2006.01)
*B28B 17/00* (2006.01)
*A61L 27/10* (2006.01)

(52) U.S. Cl.
CPC .............. *B28B 11/0854* (2013.01); *A61L 27/10* (2013.01); *B28B 17/0063* (2013.01); *A61L 2430/38* (2013.01)

(58) Field of Classification Search
CPC ........ B28B 11/0854; B28B 1/48; A61L 27/10
See application file for complete search history.

(56) References Cited

U.S. PATENT DOCUMENTS

| 1,475,561 | A | * | 11/1923 | Bath | B23D 77/00 |
| | | | | | 407/18 |
| 4,523,170 | A | * | 6/1985 | Huth, III | 336/83 |
| 5,215,693 | A | * | 6/1993 | Lee | 264/656 |
| 2005/0209698 | A1 | * | 9/2005 | Gordon et al. | 623/17.15 |
| 2006/0025866 | A1 | * | 2/2006 | Serafin et al. | 623/23.56 |
| 2010/0119846 | A1 | * | 5/2010 | Sawada | 428/426 |

\* cited by examiner

*Primary Examiner* — Erin Snelting
(74) *Attorney, Agent, or Firm* — Phillips Ryther & Winchester; Matthew D. Thayne

(57) ABSTRACT

Methods for threading ceramic materials, such as ceramic materials used for spinal implants or other biomedical implants. In some implementations, an expected rate of shrinkage of the block upon undergoing a firing process may be determined. A scaling factor may then be applied using the expected rate of shrinkage to select a tap having a size larger than a desired thread size. A green block may then be tapped with the selected tap to form a threaded opening in the green block. The block may be machined in order to remove cracks caused by the tapping process and/or to form the block into a desired shape/size. The green block may then be fired, which may result in a reduction of a size of the block and a size of the threaded opening.

22 Claims, 4 Drawing Sheets

METHODS FOR THREADING SINTERABLE MATERIALS AND RELATED APPARATUS AND SYSTEMS

RELATED APPLICATIONS

This application claims the benefit under 35 U.S.C. §119 (e) of U.S. Provisional Patent Application No. 61/721,796 filed Nov. 2, 2012 and titled "METHODS FOR THREADING SINTERABLE MATERIALS AND RELATED APPARATUS AND SYSTEMS," which application is incorporated herein by reference in its entirety.

SUMMARY

Disclosed herein are implementations of methods for threading ceramic material, such as silicon nitride ceramic material. Such methods may further comprise forming such materials into various items, such as spinal implants or other biomedical implants, for example, by way of a firing process.

In some implementations of such methods, the method may comprise inserting a ceramic powder, such as a silicon nitride ceramic powder, into a mold and compressing the ceramic powder into a block. An expected rate of shrinkage of the block upon undergoing a firing process may be determined. A tap may then be selected having a size larger than a desired thread size by applying a scaling factor using the expected rate of shrinkage. In implementations in which conditions, processes, and parameters are tightly controlled, the same scaling factor may be used in order to manufacture a number of different implants or other ceramic items.

The block may then be tapped with the selected tap to form a threaded opening in the block. The block may be machined. In some implementations, the block may be machined in order to remove cracks caused by the tapping process and/or to form the block into a desired shape/size. The ceramic block may then be fired. This firing may reduce a size of the block and reduce a size of the threaded opening. In some implementations, the step of tapping the block may be performed before the step of firing the block. In some implementations, the step of machining the block may also, or alternatively, be performed before the step of firing the block. A machining step may also be performed after firing the block if desired.

In some implementations, one or more of the machining steps may comprise removing material from the block comprising cracks formed during the step of tapping the block. For example, in some implementations, the step of machining the block may comprise identifying a thickness of a layer of material in at least one surface of the block and in which at least substantially all of the cracks formed during the step of tapping the block, and removing the layer of material having the thickness so as to remove at least substantially all of the cracks formed during the step of tapping the block.

In some implementations, the step of compressing the ceramic powder into a block may comprise using a cold isostatic pressing process to compress the ceramic powder into the block.

Spinal implants, such as intervertebral spacers, often comprise hollow interior portions. As such, in some implementations, the step of tapping the block may comprise tapping the block such that the threaded opening extends to a hollow interior of the spinal implant. Because tapping a green ceramic block may result in cracking on the exterior surface of the block, particularly near the tapped opening, material adjacent to the threaded opening within the hollow interior may be removed prior to the step of firing the block. This removal of material may be performed in addition to removing material on one or more exterior surfaces of the block comprising cracks. In this manner, the finished product after firing may be produced without cracks, or at least substantially without cracks, such that post-firing removal of cracks, which is typically much more difficult, may be avoided.

In another more particular example of a method for manufacturing a spinal implant, the method may comprise selecting a mold having a sufficient size larger than a desired size of a spinal implant so as to account for an expected shrink rate and further to account for an expected layer of cracking during a subsequent tapping process. A silicon nitride ceramic powder may be inserted into the selected mold, after which the silicon nitride ceramic powder may be compressed into a spinal implant block.

An expected shrink rate of the spinal implant block upon undergoing a firing process may be determined, and a scaling factor may be applied using the expected rate of shrinkage to select a tap having a size larger than a desired thread size. In some implementations, the scaling factor may be selected such that the selected tap has a size that is between about 19% and about 20% larger than the desired thread size. The spinal implant block may then be tapped with the selected tap to form a threaded opening in the spinal implant block.

Because cracks may be formed in the spinal implant block from the tapping process, after the tapping step, a thickness of a layer of material in at least one surface of the spinal implant block in which at least substantially all of the cracks formed during the tapping step may be identified, after which this layer(s) may be removed so as to remove at least substantially all of the cracks formed during the step of tapping the spinal implant block. After removing the cracks formed in the green state from the tapping step, the spinal implant block may be fired so as to reduce a size of the spinal implant block and also reduce a size of the threaded opening.

In another example of a method for threading a sinterable material according to some implementations, the method may comprise inserting a powder into a mold and forming the powder into a green block. In some implementations, the step of forming the powder into a green block may comprise forming a slurry comprising the powder and compressing the slurry into the green block.

An expected rate of shrinkage of the green block upon undergoing a firing process may be determined, after which a scaling factor may be applied using the expected rate of shrinkage to select a tap having a size larger than a desired size of a threaded opening in the green block after firing. The green block may be tapped with the selected tap to form a threaded opening in the green block, after which the green block may be fired to form a finished block. In some implementations, the finished block may comprise a spinal implant, such as an intervertebral spacer.

Some implementations may further comprise machining the green block and/or machining the finished block. In some implementations, the step of machining the green block may comprise identifying a thickness of a layer of material in at least one surface of the green block and in which at least substantially all of the cracks formed during the step of tapping the green block, and removing the layer of material having the thickness so as to remove at least substantially all of the cracks formed during the step of tapping the green block. In some implementations, the step of machining the green block may comprise removing a layer of material having a thickness of about 1.0 mm to about 2.0 mm from the green block.

As previously mentioned, in some implementations in which a spinal implant is formed, the step of tapping the green block may comprise tapping the green block such that the threaded opening extends to a hollow interior of the spinal implant. In some such implementations, material adjacent to the threaded opening within the hollow interior may be machined away or otherwise removed prior to the step of firing the green block.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
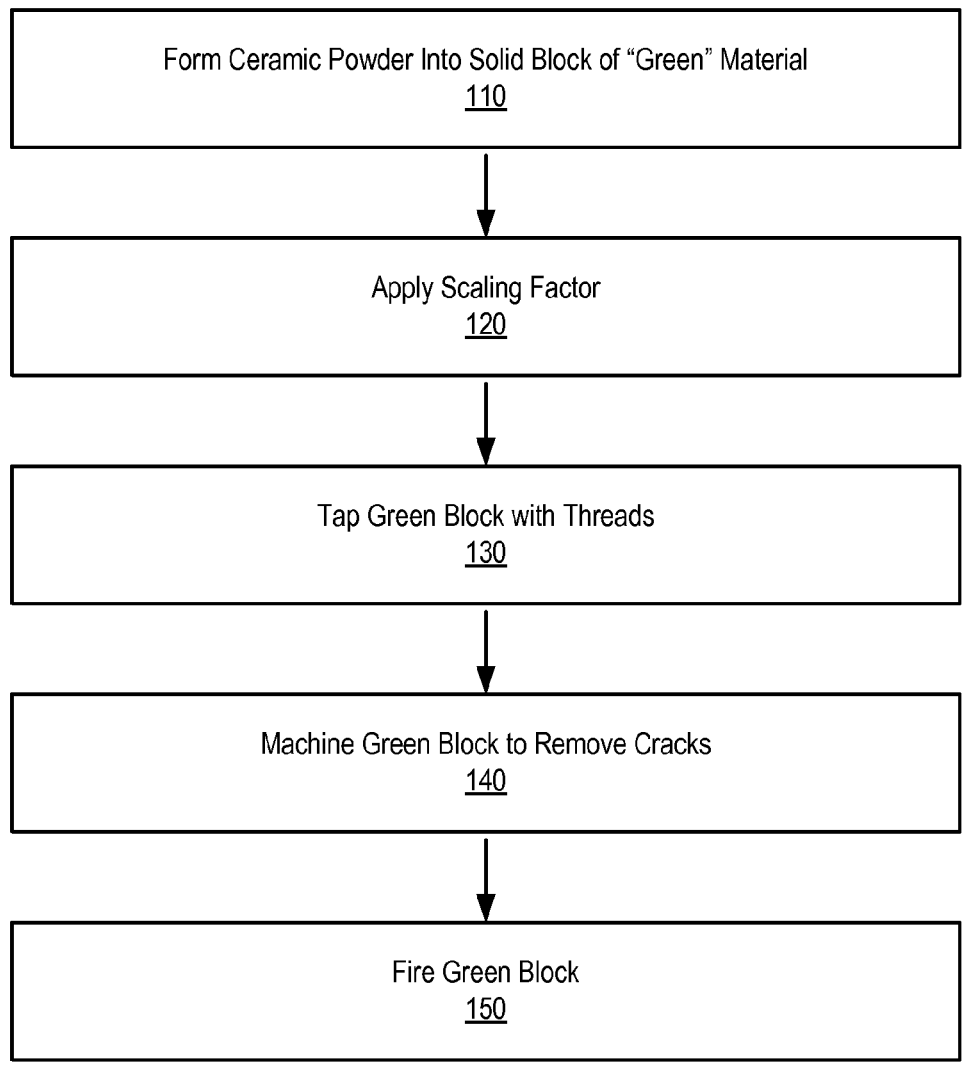
FIG. 1 is a flow chart illustrating one example of a method for manufacturing a threaded biomedical implant.

Various implementations of methods are disclosed herein for threading a sinterable material, such as silicon nitride or other ceramic materials, along with related apparatus and systems. In some implementations, the sinterable material may be suitable for use in manufacturing biomedical implants, such as spine implants, hip implants, knee implants, dental implants, and the like.

Silicon nitride ceramics have tremendous flexural strength and fracture toughness. In some embodiments, such ceramics have been found to have a flexural strength greater than about 700 Mega-Pascal (MPa). Indeed, in some embodiments, the flexural strength of such ceramics have been measured at greater than about 800 MPa, greater than about 900 MPa, or about 1,000 MPa. The fracture toughness of silicon nitride ceramics in some embodiments exceeds about 7 Mega-Pascal root meter (MPa·m$^{1/2}$). Indeed, the fracture toughness of such materials in some embodiments is about 7-10 MPa·m$^{1/2}$.

Examples of suitable silicon nitride materials are described in, for example, U.S. Pat. No. 6,881,229, titled "Metal-Ceramic Composite Articulation," which is incorporated by reference herein. In some embodiments, dopants such as alumina ($Al_2O_3$), yttria ($Y_2O_3$), magnesium oxide (MgO), and strontium oxide (SrO), can be processed to form a doped composition of silicon nitride. In embodiments comprising a doped silicon nitride or another similar ceramic material, the dopant amount may be optimized to achieve the highest density, mechanical, and/or antibacterial properties. In further embodiments, the biocompatible ceramic may have a flexural strength greater than about 900 MPa, and a toughness greater than about 9 MPa·m$^{1/2}$. Flexural strength can be measured on standard 3-point bend specimens per American Society for Testing of Metals (ASTM) protocol method C-1161, and fracture toughness can be measured using single edge notched beam specimens per ASTM protocol method E399. In some embodiments, powders of silicon nitride may be used to form the ceramic implants, either alone or in combination with one or more of the dopants referenced above.

Other examples of suitable silicon nitride materials are described in U.S. Pat. No. 7,666,229 titled "Ceramic-Ceramic Articulation Surface Implants," which is hereby incorporated by reference. Still other examples of suitable silicon nitride materials are described in U.S. Pat. No. 7,695,521 titled "Hip Prosthesis with Monoblock Ceramic Acetabular Cup," which is also hereby incorporated by reference.

Notwithstanding these advantageous characteristics of silicon nitride materials, silicon nitride and other similar ceramic materials have certain disadvantages for certain biomedical implant applications. For example, although the very high strength and toughness of silicon nitride materials make it ideal for many medical device uses, such as spinal fusion implants, these characteristics also make it difficult to thread the material, particularly for internal or female thread formation.

Indeed, it is often the case that very hard and/or tough materials with properties similar to silicon nitride ceramics can only be threaded by way of a thread grinding procedure. Such procedures are typically quite expensive and time consuming, and may be prohibitively expensive for certain applications. For example, the equipment typically used for such procedures is often highly specialized and expensive and, moreover, the process itself is often very time consuming. This is particularly the case for internal or female thread grinding, and even more so with respect to female threads that must be grinded in relatively small-diameter holes (e.g., holes having a diameter of 1/16 inch or less). There are also many technical challenges and difficulties involved in threading such materials, again, particularly for forming female threads in relatively small holes or other openings.

In order to overcome one or more of these disadvantages, in accordance with the disclosure provided herein, a process for threading a silicon nitride and/or other ceramic materials having similar properties may be employed that comprises threading the ceramic material while the material is in a "green" or unfired state. In this state, the ceramic material may be threaded much more easily and without the expensive equipment and/or processes described above because the material is much less hard, more pliable, and more easily machined in the green state. Indeed, grinding is not necessary at all. Instead, the green ceramic material may simply be tapped, which is a much less expensive, simpler, and easier process than grinding.

However, ceramic materials typically undergo substantial shrinkage during a firing stage. In other words, a block of ceramic material in its green state will typically be considerably larger than it will be after it has been fired. For example, with respect to certain silicon nitride ceramic materials, shrinkage by a factor of about 20% takes places between the green and fired states. As such, a scaling factor must be applied that corresponds with the expected shrinkage (about 20% in certain formulations of silicon nitride) that will occur during firing. This scaling factor may be applied during the tapping process (or another similar process for threading the material). Otherwise, the resulting threads will be too small. Thus, using certain formulations of silicon nitride as an example again, the thread(s) size must be scaled up by a factor of about 20% to obtain the desired threads after firing.

It may also be important for certain applications that the ingredients and processes involved in forming, molding, and firing the ceramic material be tightly controlled such that the shrinkage amount is consistent from one product to the next. For example, tight controls over shrinkage may, in some embodiments, be obtained using uniaxial or isostatic pressing of powders to a narrow density range. For example, in some embodiments, shrinkage may be tightly controlled by accurately and precisely weighing the ceramic powder to within a particular tolerance threshold. Alternatively, or additionally, a statistical process control (SPC) may be used to record, monitor, and/or otherwise control the pressed part weight and dimensions. One or more of these methods may be used to result in a control of shrinkage rates such that variance between the shrinkage of implants or other ceramic pieces after firing is within about 0.25%. In some such embodiments, the shrinkage rate amongst various implants or other ceramic pieces after firing is with about 0.15%.

Although the specific implementations and embodiments described below are, for purposes of illustration, in the context of intervertebral spacers, it is contemplated that the principles and processes described herein may be useful in a wide variety of other industries and/or with a wide variety of other products and/or apparatus. For example, a wide variety of other biomedical implants that undergo a sintering/firing process, or otherwise undergo a change in size during the course of manufacturing, may also be threaded in accordance with the principles and processes provided herein. Such biomedical implants include, for example, spine implants, hip implants, knee implants, dental implants, and the like. The principles described herein may also be useful in industries outside of biomedical implants. For example, other manufacturing and general industrial fields that utilize sintered materials that are fired or otherwise shrink from an initial stage to a finished stage may find the teachings provided herein useful.

It is also contemplated that, although many of the specific implementations and embodiments described below are described in the context of ceramic materials, the principles and processes described herein may also be useful in connection with other materials that undergo a sintering/firing stage that results in shrinkage, or another similar change in properties. For example, solid state sintering or powdered metallurgy may involve taking one or more metals in the form of a powder and compacting the powdered metal in a mold or die. The material may then be fired or heated, which may result in a finished product of a smaller size. Thus, the principles and processes described herein may be employed on such powdered metal materials. Other examples include porcelain materials, carbides, clays, and the like. Generally, the principles and processes described herein may find application in any material that may have need for threading and that undergoes a change in size during a sintering/firing or other similar process.

It has also been discovered that, for certain embodiments and implementations, it may be desirable to tap or otherwise thread the green material at a very early stage, such as before any additional machining is performed on the material. For some implementations that involve starting with a block of green material that is then machined or otherwise formed into a desired shape/configuration (hereinafter, "machined"), it has been discovered that tapping or otherwise threading the material after the block has been machined may result in cracks forming in the machined block. However, tapping or otherwise threading the block material before any machining has taken place may be useful in solving this problem because cracks that have formed near the perimeter of the pre-machined block may be removed from the block during the machining process. Such cracks may form only on the surface of the block within which the thread was formed. Thus, by removing this surface during machining, the cracked portion of the pre-fired block may be easily removed prior to firing.

It is contemplated that the removal of the cracks, as described above, may be, in some implementations, performed as part of a machining process that may serve other purposes. However, in other implementations, a step may be added to a manufacturing process specifically in order to remove cracks from a green or pre-fired block of material. In some such implementations, the block may be initially created with a larger size than would otherwise be needed. In other words, one or more of the dimensions of an initial green or pre-fired block of material may be selected as being greater than what would otherwise be warranted in order to ensure that any cracks that form as a result of tapping or otherwise threading the material can be machined away or otherwise removed prior to firing of the material. Other embodiments and implementations, however, may be of such a nature that the initial block of material need not be made larger solely for the purpose of crack removal. It may, for example, be the case that machining that would be performed for other reasons, such as forming the pre-fired block into a desirable shape, may effectively rid the block of cracks without requiring the use of additional material.

Additional details of certain embodiments and implementations will now be discussed with greater particularity with reference to the accompanying drawings. FIG. 1 is a flow chart illustrating one implementation of a method for manufacturing a threaded device, namely, a threaded intervertebral spacer.

In this implementation, a ceramic powder is formed into a solid block at step 110. In some implementations, the ceramic powder may comprise a doped silicon nitride material. In some implementations, dopants such as alumina ($Al_2O_3$), yttria ($Y_2O_3$), magnesium oxide (MgO), and/or strontium oxide (SrO) may be used. In some implementations, the ceramic powder may be formed into a solid block via a compression process, such as cold isostatic pressing. In some implementations, step 110 may comprise weighing out a desired amount of ceramic powder, including any of the ceramic materials and/or dopants disclosed herein. Step 110 may also comprise introducing the ceramic powder into an isopress mold. The mold may be of any suitable variety, and can be configured to yield the desired shape and configuration of the block. In various implementations, the mold can comprise silicone and/or urethane. In some implementations, the isopress mold may comprise a resilient material such that it can return to the original shape after having been compressed via an isostatic pressing procedure.

The ceramic powder may be tightly packed into the isopress mold. For example, in some implementations, a vibration plate or other vibration mechanism may be used to tightly pack the ceramic powder within the isopress mold. Cold isostatic pressing of the mold and powder together may be used to compact the powder into a desired shape. However, in some implementations, the ceramic powder may initially be compacted into an intermediate, or partially compacted, core, after which a cold isostatic pressing process can be used to further compress the block at a later stage. In various implementations, pressures used during the cold isostatic pressing process may be within a range of from about 1,000 psi to about 60,000 psi.

In some implementations, the size and/or shape of the solid block may be configured specifically to accommodate a later step in which cracks in the block are machined or otherwise removed from the block. For example, an additional inch of material may be added to the perimeter of the block if approximately one inch of cracking is expected and will ultimately need to be removed from the block prior to firing.

At step 120, a scaling factor is applied that corresponds with the shrinkage that is expected to take place during the firing process. In some implementations, step 120 may comprise determining to what extent the block will, or is likely to, shrink during the firing stage. For example, in the case of certain silicon nitride ceramics, about 20% of shrinkage is expected between the green state and the post-firing state. Step 120 may further comprise selecting a tap having a size that is larger than the desired thread size by about the shrinkage factor. For example, in the case of a silicon nitride intervertebral spacer, a tap may be selected that is scaled up by about 20% larger in diameter and/or pitch than the desired size of the female thread in the intervertebral implant.

In some embodiments and implementations, the shrinkage rate for a silicon nitride ceramic implant may be controlled so as to be between about 18% and about 21%. In some such embodiments and implementations, the shrinkage rate may be controlled so as to be between about 19% and about 20%. In some embodiments and implementations, the shrinkage rate for a batch of silicon nitride ceramic implants may be tightly controlled so as to be about 19.35%+/−about 0.25%. In some such embodiments and implementations, the shrinkage rate for a batch of silicon nitride ceramic implants may be tightly controlled so as to be about 19.35%+/−about 0.15%.

At step 130, the "green" block of ceramic material is tapped to form threads at a desired location in the block. For example, for implementations in which an intervertebral spacer is manufactured, the threads may be tapped or otherwise formed at an end of the block that will ultimately comprise a surface of the spacer that will be coupled with an instrument for installing the surface within an intervertebral space of a patient. In other implementations in which a dental implant is manufactured, the threads may be tapped or otherwise formed in a portion of the block that will ultimately comprise threads for coupling a dental bone anchor with another dental implant, such as an anchor abutment. Such a dental bone anchor may be configured to be integrated with and affixed to a patient's oral bone cavity on one side, and may provide a surface for integration with the anchor abutment on the other side. The anchor abutment may protrude above the epithelial tissue of a patient's oral cavity, and may provide a substrate for positioning and fixation of dental crowns, bridges, and the like.

At step 140, the tapped green block is machined in order to remove cracks that, in some implementations, may be formed during step 130. In certain implementations, these cracks form solely, or at least primarily, on the surface of the green block. As such, by removing enough of the surface of the green block, these cracks may be removed prior to the firing steps, after which they would be much more difficult to remove. In some implementations, step 140 may comprise removal of about 1.0 to about 2.0 mm of material from the surface of the tapped green block. In some implementations, step 140 may further comprise machining the tapped green block in order to achieve a desired final shape. In some implementations, the machining step may remove the cracks as part of the machining process for achieving the desired final shape. In other implementations, two separate machining steps may be performed, one of which removes the cracks and the other of which is performed to form the block into a desired shape/size.

As mentioned above, the removal of the cracks in step 140 may be performed as part of a machining process that may serve other purposes. For example, machining may take place in order to form the green block into a desired shape/size. As part of this machining, any cracks that may have been created during the tapping process at step 130 may also be removed. However, in other implementations of the process depicted in FIG. 1, step 140 may be performed with the sole purpose of removing cracks from the green block and additional machining or other processing, if necessary, may be done before or after step 140.

In some such implementations, the green block may be initially created with a larger size than would otherwise be needed. In other words, one or more of the dimensions of the green block may be initially greater than what would otherwise be desired or needed such that any cracks that form as a result of tapping the green block can be machined away or otherwise removed prior to firing of the material without compromising the desired dimensions of the final product.

In some embodiments, an internal cavity may also be formed within the block. For example, in embodiments in which the block is to become a spinal implant, it may be desirable to form a hollow interior for facilitating bone growth in an intervertebral region. In some such embodiments, it may be desirable to remove a layer of material from the internal cavity following tapping of the green block as well. For example, in embodiments in which a threaded opening extends all of the way from an exterior surface of the implant to the hollow cavity/interior, cracks may form during step 130 at surfaces adjacent to both ends of the tapped opening. As such, in some implementations step 140 may further comprise removing a layer of material from a hollow interior portion of the green block to remove cracks.

Finally, at step 150, the green block is fired. The green block may be fired in any suitable manner. For example, the green block may be fired by way of sintering, hot isostatic pressing, or the like.

Figure 2:
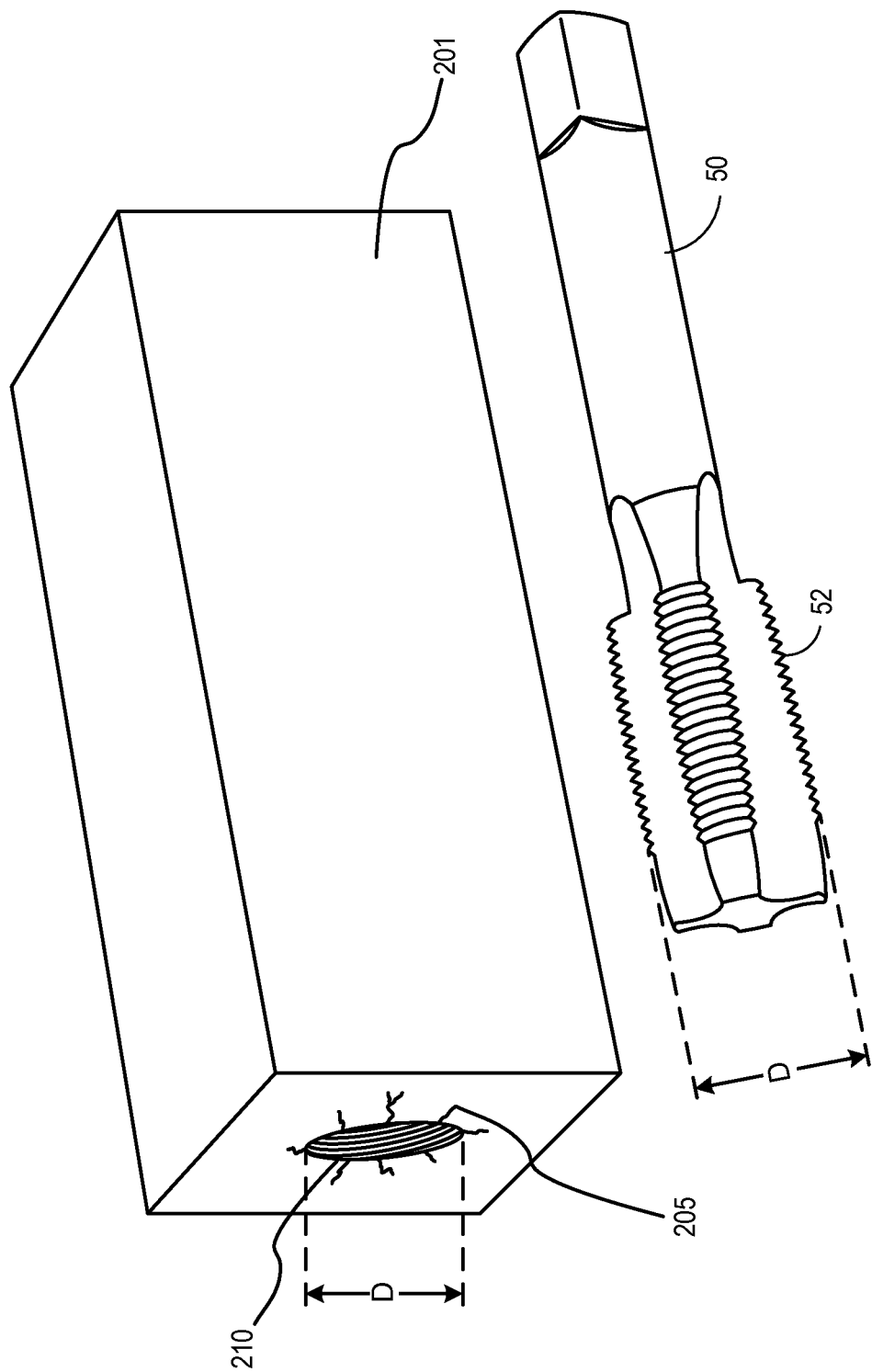
FIG. 2 illustrates a perspective view of an embodiment of a block of ceramic material in a green state having a threaded opening.

FIG. 2 depicts an example of a green block 201 of a ceramic material, such as a silicon nitride ceramic material. Block 201 will eventually be formed into an intervertebral spacer, as discussed below. Block 201 comprises a threaded opening 210. Threaded opening 210 may be formed using tap 50 that comprises tap threads 52. In some embodiments, a pilot hole may be milled into green block 201 prior to using tap 50. As also illustrated in FIG. 2, threaded opening 210 has a major diameter "D." Since threads 52 of tap 50 were used to form threaded opening 210, threads 52 have a major thread diameter that at least substantially matches diameter D.

As described above, diameter D may be selected using a scaling factor that corresponds with the expected shrinkage that will occur during firing. Thus, in embodiments comprising certain silicon nitride compositions, tap 50 may be selected such that the major thread diameter is about 10% to about 30% larger than the desired thread diameter of threaded opening 210 after green block 201 has been fired. In some such embodiments, tap 50 may be selected such that the major thread diameter is about 20% larger than the desired thread diameter of threaded opening 210 after green block 201 has been fired.

FIG. 2 also illustrates that block 201 comprises cracks 205. As described elsewhere herein, cracks 205 may be formed during the process of tapping or otherwise forming threaded opening 210 in block 201. As illustrated in the figure, cracks 205 begin around the threaded opening of block 201 and do not extend all of the way into the center of the block. As such, cracks 205 may be machined or otherwise removed while block 201 is still in a green or unfired state.

Figure 3:
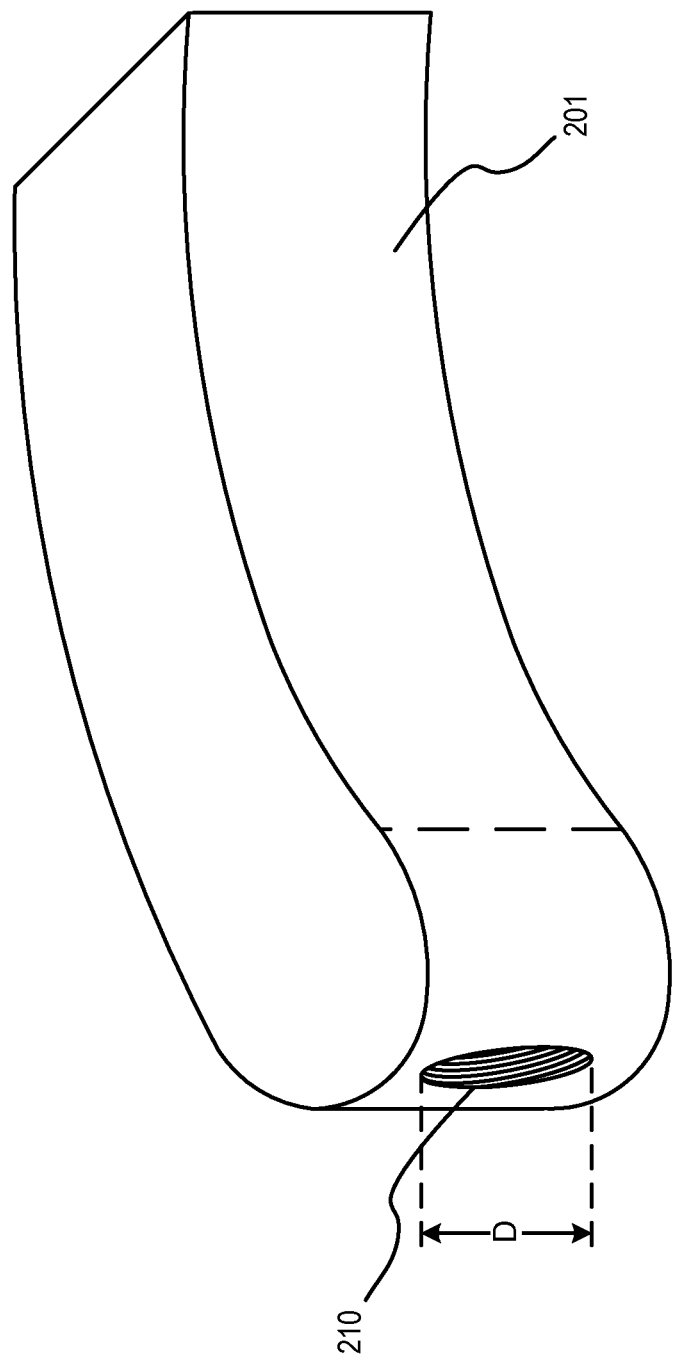
FIG. 3 illustrates a perspective view of the block of ceramic material of FIG. 2 after a machining step has been performed.

FIG. 3 illustrates block 201 after a machining step has been performed. In FIG. 3, block 201 is still in a green state. As such, threaded opening 210 still has a diameter D. However, as illustrated in the figure, block 201 has been formed into a desired shape suitable for use as an intervertebral spacer during a machining step. Block 201 also no longer comprises cracks 205. Cracks 205 may be removed during the machining step referenced above, in which block 201 was formed into a shape suitable for placement in an intervertebral space of a patient. However, other embodiments are contemplated in which a step/process is performed solely for purposes of removing cracks 205.

Figure 4:
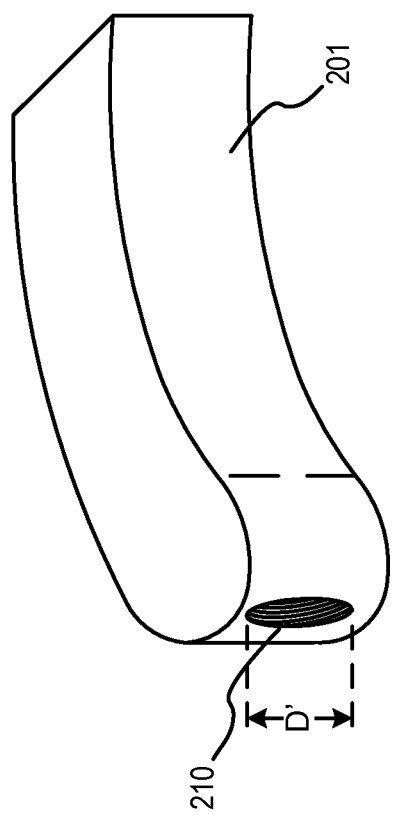
FIG. 4 illustrates a perspective view of the block of ceramic material of FIG. 2-3 after a firing step.

FIG. 4 illustrates block 201 after it has been fired or sintered. In FIG. 4, block 201 comprises a spinal implant. More particularly, block 201 comprises an intervertebral spacer that may be provided for implantation into the space between a pair of adjacent vertebrae of a patient. Such spinal implants may be installed following removal of disc material between endplates of the adjacent vertebrae to maintain the adjacent vertebrae in a predetermined and substantially fixed spaced relation while promoting bone growth and fusion.

In other embodiments, block 201 may be machined or formed for use in connection with other biomedical implants, such as spine implants, hip implants, knee implants, dental implants, and the like. In still other embodiments, block 201 may be machined or formed for use in other industrial applications, including any devices or components made up of a ceramic or other sinterable material having a threading or threaded component.

Threaded opening 210 in FIG. 4 has a diameter D', which is smaller than diameter D by the scaling factor. Thus, for example, for certain silicon nitride ceramic compositions, D' may be about 0.8 of D. Threaded opening 210 may be configured to facilitate coupling of spinal implant 201 with an instrument for installing spinal implant 201 within an intervertebral space.

Although not depicted in the figures, it should be understood that spinal implant 201 may be machined or otherwise formed with a variety of other features, components, or characteristics that may be useful for spinal implants. Such steps may take place before firing, and other such steps may take place after firing. For example, some embodiments may be formed with a tapered or lordotic cross section to substantially conform to the curvature of the intervertebral space. The superior and inferior surfaces of the implant 201 may also comprise ridges, teeth, spikes or other engagement features to facilitate desired engagement with adjacent vertebrae. Spinal implant 201 may also comprise one or more recesses or bores. Such recesses/bores may be positioned on one or more surfaces of spinal implant 201, such as the superior and inferior surfaces, or on one or more side surfaces. Such recesses/bores may be configured for receiving and supporting an osteoconductive bone graft material, such as allograft or autograft bone material. One or more of these openings may be provided that extend through both the superior and inferior surfaces of the implant.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Throughout this specification, any reference to "one embodiment," "an embodiment," or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, inventive aspects lie in a combination of fewer than all features of any single foregoing disclosed embodiment. It will be apparent to those having skill in the art that changes may be made to the details of the above-described embodiments without departing from the underlying principles set forth herein. The scope of the present invention should, therefore, be determined only by the following claims.

The invention claimed is:

1. A method for threading a ceramic material, the method comprising the steps of:
 inserting a ceramic powder into a mold;
 compressing the ceramic powder into a block;
 determining an expected rate of shrinkage of the block upon undergoing a firing process;
 applying a scaling factor using the expected rate of shrinkage to select a tap having a size larger than a desired thread size;
 tapping the block with the selected tap to form a threaded opening in the block;
 machining the block by removing material from the block comprising cracks formed during the step of tapping the block, wherein the step of machining the block comprises:
  identifying a thickness of a layer of material in at least one surface of the block comprising at least substantially all of the cracks formed during the step of tapping the block; and
  removing the layer of material having the thickness so as to remove at least substantially all of the cracks formed during the step of tapping the block; and
 firing the block, wherein the firing reduces a size of the block and reduces a size of the threaded opening, wherein the step of machining the block is performed before the step of firing the block, and wherein the step of tapping the block is performed before the step of firing the block.

2. The method of claim 1, wherein the step of identifying a thickness comprises identifying a thickness of a layer of material in at least one surface of the block comprising all of the cracks formed during the step of tapping the block; and wherein the step of removing the layer comprises removing the layer of material having the thickness so as to remove all of the cracks formed during the step of tapping the block.

3. The method of claim 1, wherein the ceramic powder comprises a silicon nitride ceramic powder.

4. The method of claim 1, wherein the step of compressing the ceramic powder into a block comprises using a cold isostatic pressing process to compress the ceramic powder into the block.

5. The method of claim 1, wherein the block comprises a spinal implant.

6. The method of claim 5, wherein the step of tapping the block comprises tapping the block such that the threaded opening extends to a hollow interior of the spinal implant.

7. The method of claim 6, further comprising removing material adjacent to the threaded opening within the hollow interior prior to the step of firing the block.

8. A method for manufacturing a spinal implant, the method comprising the steps of:
 selecting a mold having a sufficient size larger than a desired size of a spinal implant so as to account for an expected shrink rate and further to account for an expected layer of cracking during a subsequent tapping process;
 inserting a silicon nitride ceramic powder into the selected mold;

compressing the silicon nitride ceramic powder into a spinal implant block;

determining an expected shrink rate of the spinal implant block upon undergoing a firing process;

applying a scaling factor using the expected rate of shrinkage to select a tap having a size larger than a desired thread size, wherein the scaling factor is selected such that the selected tap has a size that is between about 19% and about 20% larger than the desired thread size;

tapping the spinal implant block with the selected tap to form a threaded opening in the spinal implant block, whereby cracks are formed in the spinal implant block from the tapping process;

identifying a thickness of a layer of material in at least one surface of the spinal implant block in which at least substantially all of the cracks formed during the step of tapping the spinal implant block are present;

removing the layer of material having the thickness so as to remove at least substantially all of the cracks formed during the step of tapping the spinal implant block; and firing the spinal implant block after the step of removing the layer of material and after the step of tapping the spinal implant block, wherein the firing reduces a size of the spinal implant block and reduces a size of the threaded opening.

9. The method of claim 8, wherein the step of identifying a thickness comprises identifying a thickness of a layer of material in at least one surface of the spinal implant block in which all of the cracks formed during the step of tapping the spinal implant block are present, and wherein the step of removing the layer comprises removing the layer of material having the thickness so as to remove all of the cracks formed during the step of tapping the spinal implant block.

10. A method for threading a sinterable material, the method comprising the steps of:

inserting a powder into a mold;

forming the powder into a green block;

determining an expected rate of shrinkage of the green block upon undergoing a firing process;

applying a scaling factor using the expected rate of shrinkage to select a tap having a size larger than a desired size of a threaded opening in the green block after firing;

tapping the green block with the selected tap to form a threaded opening in the green block;

identifying a thickness of a layer of material in at least one surface of the green block, the layer comprising at least substantially all cracks formed during the step of tapping the green block;

removing the layer of material having the thickness so as to remove at least substantially all of the cracks formed during the step of tapping the green block; and firing the green block to form a finished block.

11. The method of claim 10, wherein the step of forming the powder into a green block comprises:

forming a slurry comprising the powder; and compressing the slurry into the green block.

12. The method of claim 11, wherein the step of removing the layer of material comprises removing a layer of material having a thickness of about 1.0 mm to about 2.0 mm from the green block.

13. The method of claim 10, further comprising machining the green block.

14. The method of claim 13, wherein the step of identifying a thickness comprises identifying a thickness of a layer of material in at least one surface of the green block, the layer comprising all cracks formed during the step of tapping the green block, and wherein the step of removing the layer comprises removing the layer of material having the thickness so as to remove all of the cracks formed during the step of tapping the green block.

15. The method of claim 10, further comprising machining the finished block.

16. The method of claim 10, wherein the powder comprises a silicon nitride ceramic powder.

17. The method of claim 10, wherein the finished block comprises a spinal implant.

18. The method of claim 17, wherein the step of tapping the green block comprises tapping the green block such that the threaded opening extends to a hollow interior of the spinal implant.

19. The method of claim 18, further comprising removing material adjacent to the threaded opening within the hollow interior prior to the step of firing the green block.

20. A method for threading a ceramic material, the method comprising the steps of:

inserting a ceramic powder into a mold;

compressing the ceramic powder into a block comprising a spinal implant;

determining an expected rate of shrinkage of the block upon undergoing a firing process;

applying a scaling factor using the expected rate of shrinkage to select a tap having a size larger than a desired thread size;

tapping the block with the selected tap to form a threaded opening in the block such that the threaded opening extends to a hollow interior of the spinal implant;

machining the block by removing material from the block comprising cracks formed during the step of tapping the block;

firing the block, wherein the firing reduces a size of the block and reduces a size of the threaded opening, and wherein the step of tapping the block is performed before the step of firing the block; and removing material adjacent to the threaded opening within the hollow interior prior to the step of firing the block.

21. The method of claim 20, wherein the step of machining the block comprises:

identifying a thickness of a layer of material in at least one surface of the block comprising at least substantially all of the cracks formed during the step of tapping the block; and removing the layer of material having the thickness so as to remove at least substantially all of the cracks formed during the step of tapping the block.

22. The method of claim 20, wherein the step of machining the block is performed before the step of firing the block.

* * * * *